United States Patent
Schemmer

(10) Patent No.: US 7,802,989 B2
(45) Date of Patent: *Sep. 28, 2010

(54) OZONE TRAY

(75) Inventor: Jurgen H. Schemmer, King City (CA)

(73) Assignee: CurOzone Ireland Ltd., Dublin (IE)

( * ) Notice: Subject to any disclaimer, the term of this patent is extended or adjusted under 35 U.S.C. 154(b) by 10 days.

This patent is subject to a terminal disclaimer.

(21) Appl. No.: 12/173,433

(22) Filed: Jul. 15, 2008

(65) Prior Publication Data

US 2008/0274438 A1    Nov. 6, 2008

Related U.S. Application Data

(63) Continuation-in-part of application No. 11/590,185, filed on Oct. 31, 2006, now Pat. No. 7,413,437, which is a continuation of application No. 11/393,471, filed on Mar. 30, 2006, now Pat. No. 7,344,374, which is a continuation of application No. 10/819,415, filed on Apr. 6, 2004, now Pat. No. 7,021,931, which is a continuation of application No. 10/246,105, filed on Sep. 18, 2002, now Pat. No. 6,743,016, which is a continuation of application No. 09/712,611, filed on Nov. 13, 2000, now Pat. No. 6,454,566.

(51) Int. Cl.
  *A61C 5/00*  (2006.01)
(52) U.S. Cl. ...................................... 433/215
(58) Field of Classification Search ............. 433/80–82, 433/88, 215, 216, 223; 601/164
  See application file for complete search history.

(56) References Cited

U.S. PATENT DOCUMENTS

| | | | | | |
|---|---|---|---|---|---|
| 3,516,402 | A | * | 6/1970 | Toth | 601/164 |
| 4,021,921 | A | * | 5/1977 | Detaille | 433/81 |
| 4,438,100 | A | * | 3/1984 | Balslev et al. | 424/537 |
| 5,928,187 | A | * | 7/1999 | Glukhov et al. | 604/23 |
| 7,118,377 | B2 | * | 10/2006 | Inoue et al. | 433/80 |

* cited by examiner

*Primary Examiner*—Cris L Rodriguez
*Assistant Examiner*—Sunil K Singh
(74) *Attorney, Agent, or Firm*—Walter A. Hackler

(57) ABSTRACT

Apparatus for the treatment of iatrogenic enamel damage includes a tray for connection to a handpiece for delivering ozone to teeth. A port in the tray is provided for receiving the ozone. The tray includes a resilient edge for sealably engaging the tooth/gums to prevent escape of ozone therepast.

2 Claims, 4 Drawing Sheets

OZONE TRAY

The present application is a continuation-in-part of U.S. Ser. No. 11/590,185 filed Oct. 31, 2006, now U.S. Pat. No. 7,413,437, which is a continuation of U.S. Ser. No. 11/393,471 filed Mar. 30, 2006 now U.S. Pat. No. 7,344,374 which is a continuation of U.S. Ser. No. 10/819,415 filed Apr. 6, 2004 now U.S. Pat. No. 7,021,931 which is a continuation of U.S. Ser. No. 10/246,105 filed Sep. 18, 2002 now U.S. Pat. No. 6,743,016 which is a continuation of U.S. Ser. No. 09/712,611, filed Nov. 13, 2000, now U.S. Pat. No. 6,454,566.

The present invention generally relates to the treatment of dental caries, and more particularly is directed to apparatus for the treatment of white spot lesions utilizing an oxidizing gas.

The role of specific micro-organism such as, for example, streptococcus mutants in dental caries is well documented. Enzymes produced by such micro-organisms synthesize dextran from the sucrose passing through the mouth with food or drink resulting in the formation of dental plaque and dental caries.

Dental caries is the decay of teeth caused by demineralization of the enamel surface with organic acids produced by bacteria which adhere to teeth surfaces.

It is known that there are signs of dissolution of outer enamel tooth surfaces after a short time subsequent to placing of an orthodontic band on teeth, which, in time, creates plaque stagnation areas.

It has been confirmed that patients undergoing orthodontic therapy are susceptible to dental carries. In fact, the incidence of decalcification follows a course of fixed appliance thereby, lasting two years, may be as high as 50%.

The iatrogenic enamel damage during orthodontic treatment suggests a need for preventative programs. The present invention fills that need.

SUMMARY OF THE INVENTION

Apparatus in accordance with the present invention provides for a tray for the treatment of multiple teeth using a source of ozone gas with a handpiece for delivering the ozone to the tray and teeth. The tray receives ozone from an attachable handpiece and exposes the tooth to the ozone.

More particularly, the tray includes a resilient elastomeric material molded to substantially conform to the patient's upper or lower teeth and adjacent gums. A cavity in the molded material is provided for generally conforming to the teeth and includes subtending cavity walls for positioning on a patient's gum line as the cavity is disposed onto the teeth. A port, in communication with said cavity, provides for the introduction and evacuation of ozone.

The tray cavity may be arched, for example, the cavity may match a full arch of the patient's teeth and gums and be sized to accommodate in situ orthodontic bands or braces disposed on the teeth.

Still more particularly, the port may be centered in said tray for uniformally introducing ozone over the full arch of said cavity.

A web interconnecting inside wall of the cavity may be provided to prevent escape of the ozone and contact with tissue not to be treated.

The tray may also include a resilient edge for sealably engaging the teeth and gums to prevent escape of the gas therepast. Alternatively, a suitable sealant may be utilized for providing the sealed engagement between the tray and the teeth/gums. This enables a totally closed system for the application of the ozone to the teeth/gums.

BRIEF DESCRIPTION OF THE DRAWINGS

The advantages and features of the present invention will be better understood by the following description when considered in conjunction with the accompanying drawings, in which.

DETAILED DESCRIPTION

Figure 1:
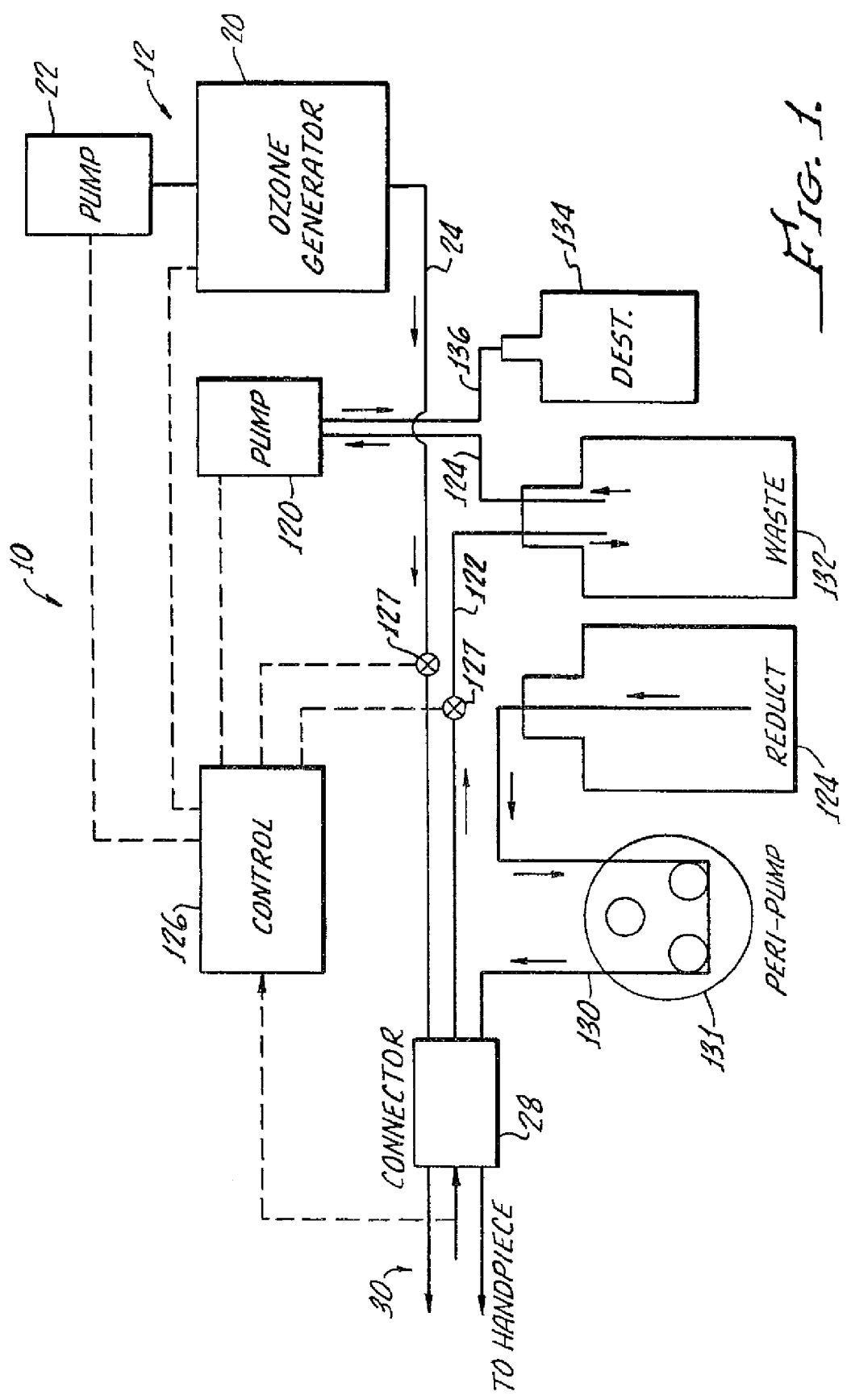
FIG. 1 illustrates a block diagram of apparatus for providing ozone, apparatus generally including a source of oxidizing gas, an aspiration pump, a source of reductant, a reductant pump and a controller for providing the oxidizing gas to a handpiece.
Figure 2:
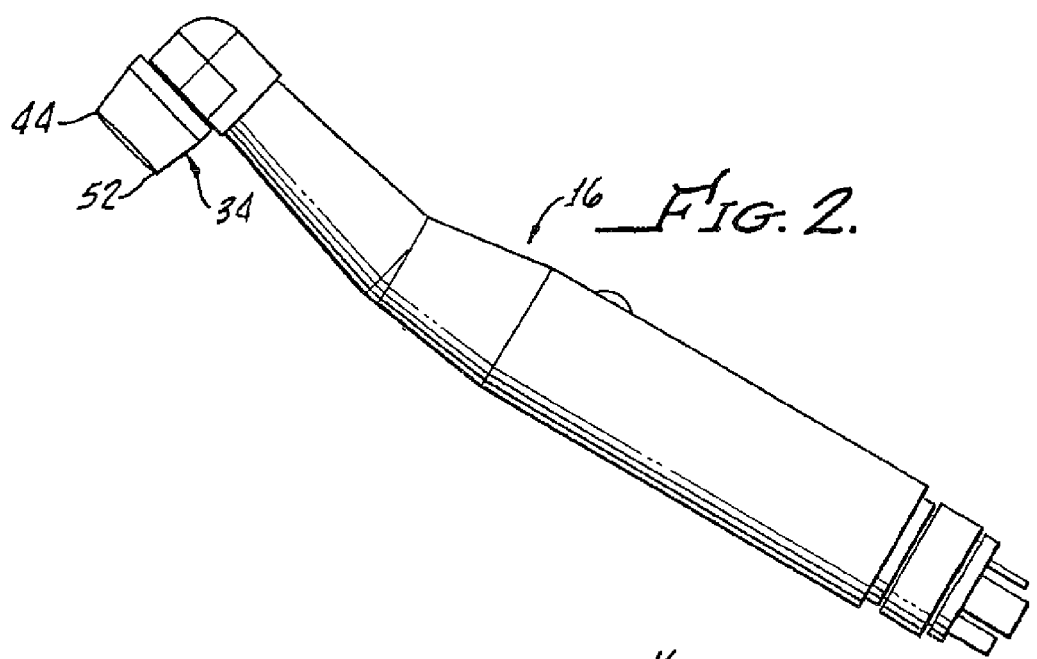
FIG. 2 illustrates a handpiece for delivering ozone to a tooth via a tray and generally showing, in this embodiment, a cup attached to the handpiece for receiving gas.
Figure 3:
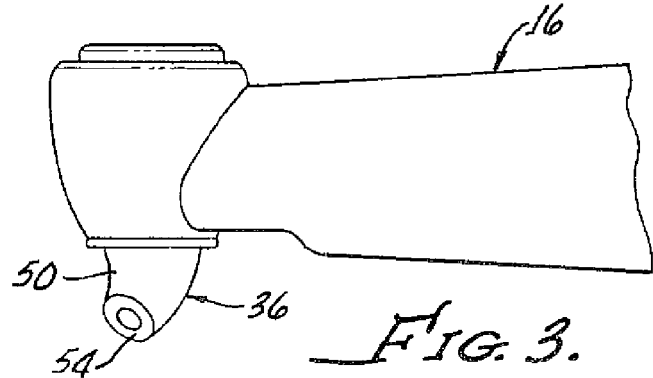
FIG. 3 illustrates the handpiece with an alternative cup embodiment, the alternative embodiment cup having an arcuate shape for facilitating application of oxidizing gas to a tooth.

With reference to FIGS. 1-4, there is shown apparatus 10 for providing ozone which includes a source 12 of ozone, and a handpiece 16 (see FIG. 2) for delivering the gas to a tooth, not shown in FIGS. 1-3. The effectiveness of an oxidizing gas such as ozone is set forth in U.S. Pat. No. 6,409,508 entitled "Use of Ozone For The Treatment of Dental Caries" by Edward Lynch. This patent is incorporated herewith in its entirety including all specification and drawings by this specific reference thereto. Specifically, incorporated is the use of pure ozone or ozonised air in a shrouded microorganism free aqueous medium such as water optimally containing a reductant.

As illustrated in FIG. 1, the ozone source 12 includes an ozone generator 20 and an ozone pump 22 for supplying ozone through a line 24, a connector 28 and lines 30 to the handpiece 16. As used herein, the term "ozone" is intended to embrace any suitable oxidizing gas, pure ozone, ionized air and other ozone gaseous mixtures.

As shown in FIGS. 2-3, cups 34, 36 attached to the handpiece 16 are provided for receiving the gas and exposing a selected area 38 on a tooth 40, see FIG. 3. The cup 34 may be attached to the handpiece 16 in any conventional manner and include a resilient edge, or sidewall, 44 for sealable engaging the tooth 40 to prevent the escape of gas therepast.

Figure 4:
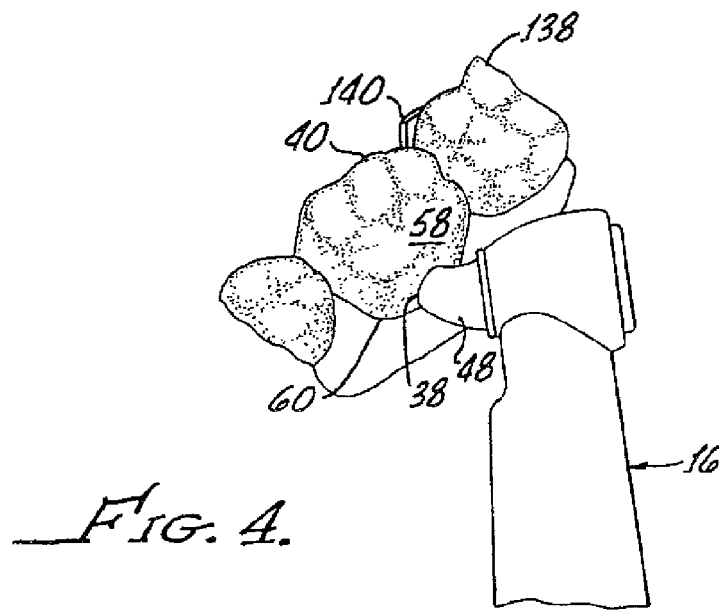
FIG. 4 is a diagram showing application of oxidizing gas to a tooth between a cusp and a gingival utilizing the handpiece and cup shown in FIG. 3.

Many different sized and shaped cups may be utilized, as for example shown in FIG. 3 the cup 36 includes an arcuate, or arched, trunk 50 to facilitate the placement of the cup 36 over the selected area 38 as shown in FIG. 4. The cups 34, 36 may have relatively uniform perimeters 52, 54 for sealably engaging the tooth 40 between a cusp 58 and a gingiva 60 as shown in FIG. 4.

Figure 6:
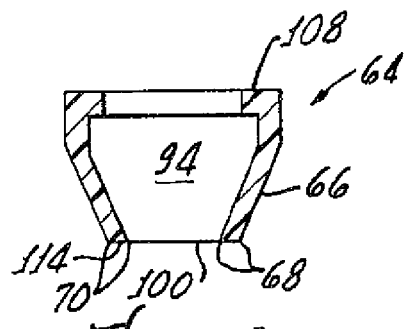
FIG. 6 is a cross sectional view an alternative embodiment of a cup for exposing a selected area of a tooth oxidizing gas.

A further cup embodiment 64 is shown in cross-section in FIG. 6 includes a tapered sidewall 66 that may be used for application of oxidizing gas to a smaller selected area (not shown) on the tooth 40.

While a resilient edge or sidewall may be used to couple the cup to the selected area 38 on the tooth 40, it should be appreciated that a separate sealant 68 (See FIG. 6) may be utilized for providing a sealable engagement between the cup 64 and the tooth 40. In this instance, the sidewall 66 need not be resilient.

Figure 7:
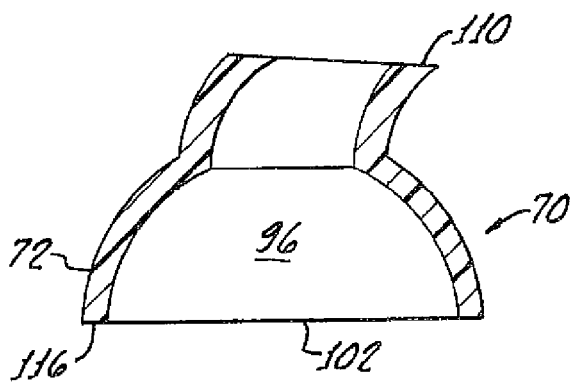
FIG. 7 is a cross sectional diagram showing an alternative embodiment of a cup in accordance with the present invention for exposing adjacent teeth to oxidizing gas.
Figure 8:
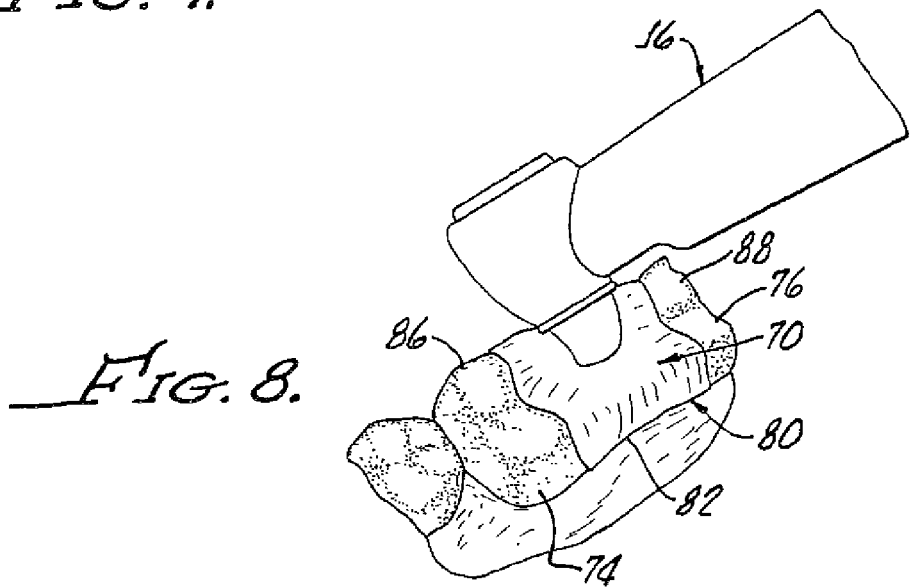
FIG. 8 illustrates the use of the cup shown in FIG. 7 as it may be applied to adjacent teeth.

Another embodiment of a cup 70 is shown in cross-section in FIG. 7 which includes walls 72 which are contoured for enabling the sealable engagement with adjacent teeth 74, 76 as shown in FIG. 8. As shown in FIG. 8, a cup edge 80 has a perimeter contour 82 for providing a sealable engagement with cups 86, 88 of adjacent teeth 74, 76.

Figure 5:
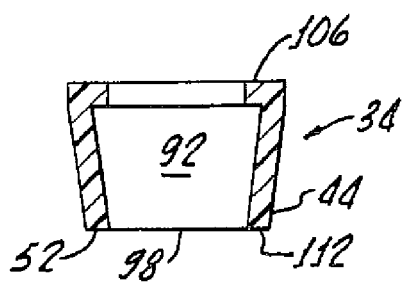
FIG. 5 is cross-sectional view of the cup shown in FIG. 2 that is suitable for use in the present invention.

All of the cups 34, 64, 70, cross-sectionally illustrated in FIGS. 5-7 include cup chambers 92, 94, 96 that subtend cup edges 98, 100, 102. As shown, each of the cups 36, 64, 70 includes walls 44, 66, 72 that define the chambers 92, 94, 96 and include first perimeters 106, 108, 110 for sealably coupling the walls 44, 66, 72 to the handpiece 16. Second perimeters 112, 114, 116 provide for coupling the walls 44, 66, 72 to the tooth 40 and exposing the selected areas 38 to gas circulated in the chambers 92, 94, 96.

As shown in FIG. 6, the embodiment 64 the first perimeter 108 may be larger than the second perimeter 115 or, as shown in FIG. 7, the first perimeter 110 may be smaller than the second perimeter 116. Accordingly, this variation in cup 64, 70 design enables the application of oxidizing gas the any number of tooth contours and to the application of oxidizing gas to a plurality of teeth as hereinabove described.

Figure 9:
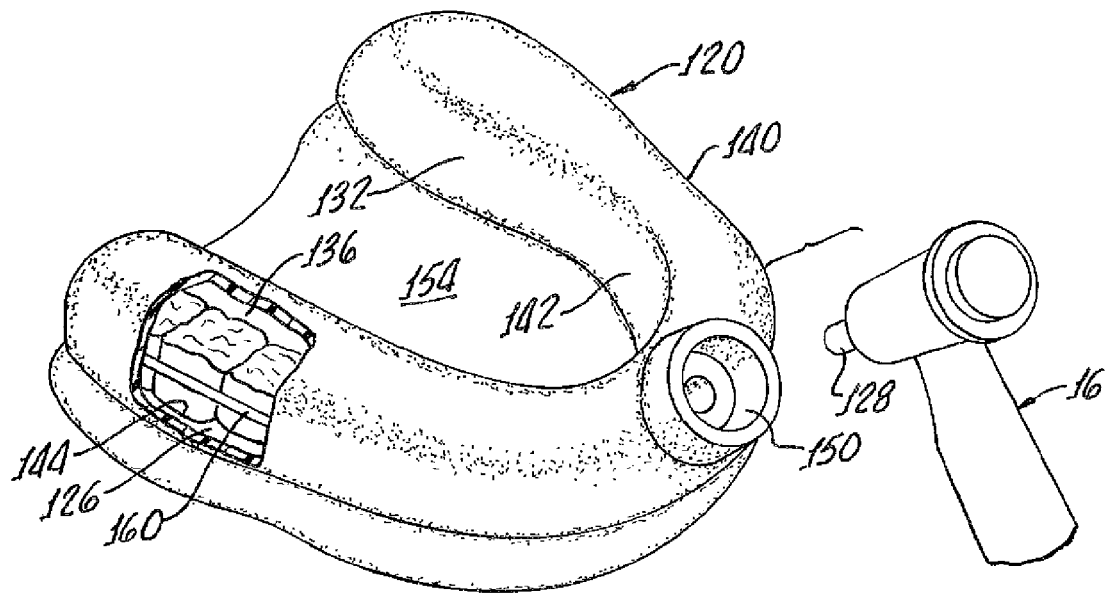
FIG. 9 is a perspective view of yet another embodiment in accordance with the present invention showing a tray for enabling application of ozone to teeth and adjacent gums of a patient with in situ orthodontic bands.
Figure 10:
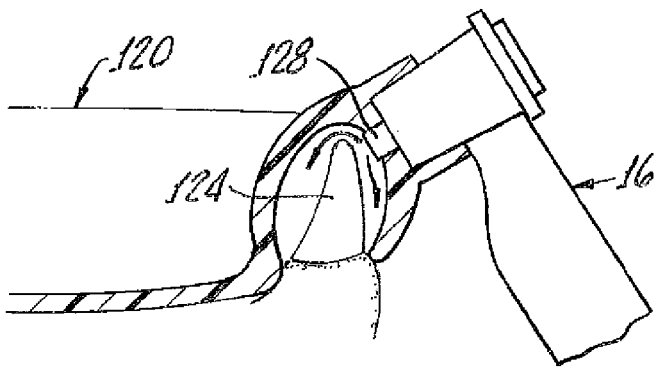
FIG. 10 illustrates handpiece engagement with a port in the tray shown in FIG. 9.

With reference to FIGS. 9 and 10, there is shown a tray 120 in accordance with the present invention for enabling application of ozone to teeth 124 and adjacent gums 126 by coupling to the handpiece 16 through a nozzle 128.

The tray 120 is formed from a resilient elastomeric material which is molded to substantially conform to the patient's upper teeth (not shown) or lower teeth 124 and the adjacent gums 126. The tray 120 may be molded in a conventional manner to perfectly conform to the teeth 124 or, alternatively, a plurality of trays 120 of different convenient sizes may be provided.

The tray 120 includes an arch 132 to effect the conforming fit. Any suitable resilient material acceptable in the dental field may be utilized.

The tray 120 is formed, or molded, with a cavity 136 with subtending walls 140, 142 for positioning on or over a gum line 144.

A port, 150 molded into the tray, communicates with the cavity 136 for the introduction and evacuation ozone through the nozzle 128 of the handpiece, as illustrated in FIG. 10.

Preferably, the port 150 is centered in the tray 120 as illustrated in FIG. 9 for uniformly introducing ozone over the full arch 132 of the cavity.

A web 154 interconnects walls 142 and walls 140 may have resilient edges 156 for sealably engaging the gums 126 to prevent escape of ozone therepast and provide a totally closed system for application and evacuation of ozone.

As illustrated in FIG. 9, the present invention further encompasses a method for the treatment of white spots cause by orthodontic bands 160. The method includes disposing the resilient elastomeric tray over the teeth 124 and orthodontic bands 160 applied thereto.

Ozone introduced into the cavity 136 via the port 150 is provided for a period of time to treat the white spots and sterilize the orthodontic bands 160.

Thereafter, the ozone is evacuated from the cavity 136 via the nozzle 128 and the tray 120 is removed from the arched upper or lower teeth 124.

With reference again to FIG. 1, the apparatus 12 includes an aspiration pump 120 and lines 30, 122, 124 connected to the handpiece 16 for enabling circulation of the ozone into and out of the cup chambers 92, 94, 96.

A controller 126, which may be of any conventional circuit design, is provided for regulating the ozone and aspiration pumps 22, 120 in order to circulate the gas into and out of the cup chambers 92, 94, 96 at a pressure insufficient to permit escape of the gas past a sealed engagement between the cups 34, 64, 70 and teeth 40, 86, 88. Control of the gas flows may also be effected through valves 130, 132 regulated by the controller 126.

Additionally, the apparatus 10 may include an aqueous reductant source 124, which is in fluid communication with the cup chambers 92, 94, 96 through lines 30, 130, and a parastalic pump 132. The reductant optionally contained in an aqueous medium, may be thiocyanate or peppermint, is utilized to flush the cup chambers 92, 94, 96 of oxidizing gas and alternatively used as a shroud for the ozone within the cup. The oxidizing gas is flushed into the aspiration line 122 following ozone treatment of the tooth 40, 86, 88. The reductant is then aspirated through line 122 and into a waste accumulator 132.

Any residual ozone is then aspirated from the accumulator 132 through the line 124 and into a canister 134 through line 136 for final elimination of the ozone. Thus, the apparatus 12 provides for a totally closed system for the application and removal of ozone to and from teeth 40, 86, 88.

It should also be appreciated that when the cups 34, 36, 64 are utilized between teeth 40, 138 (not shown in FIG. 4) a separate dam 140 may be utilized as necessary to enable cups 34, 36, 64 (not shown in FIG. 4) to sealably enclose a selected area for treatment between the teeth 40, 138.

EXAMPLE 1

Ozone Detection (ppm) Around the Cup Using a Ozone Analyser After Either 10 or 20 s of Ozone Application in vivo Study or Test: Ozone Detection (ppm) Around the Cup 34 Using a Ozone Analyser after Either 10 or 20 s of Ozone Application In Vivo Purpose: To assess the maximum ozone detectable level (ppm) around the cup 34 after either 10 s or 20 s of ozone application in vivo.

Study or Test Protocol; 20 primary root carious lesions (PRCLs) were randomly selected when the cross-sectional study was conducted. The tip of the sensor was always held within 2 mm of the edge of the cup, positioned half way between the mesial and occlusal sides of the cup. The maximum ozone detectable level (ppm) around the cup from the extracted teeth using an ozone analyser after 10 s of ozone application. The ozone analyser used was an API 450 model available from ENVIRO Technologys, UK, and was calibrated by the supplier within the previous week of delivery and this device was not used for any other purpose other than this study in the interim.

Overlying plaque was then removed using a hand held standard fine nylon fibre sterile toothbrush with water as a lubricant. Each tooth was dried using dry sterile cotton wool rolls and a dental 3 in 1-air syringe. The excavator blade was used to traverse the lesion in line with long axis of the tooth across the maximum gingival/occlusal dimension. Half of each lesion was removed using a sterile excavator. Subsequently, the remaining lesion was exposed to the ozone gas for a period of either 10 s or 20 s at room temperature (23° C.) and maximum detectable ozone level was also measured using this ozone analyser.

Test Results:

The maximum ozone detectable level (ppm) around the cup from lesions for a period of either 10 s (Table 1 and FIG. 1) or 20 s (Table 2 and FIG. 2) ozone application during the treatment of root carious lesions were as follows:

TABLE 1

Maximum ozone detectable level (ppm) after a 10 s of ozone application

| Teeth types | Sites | Ozone detection (10 s) |
|---|---|---|
| Upper left incisor | Mesial | 0.066 |
| Upper right 1. premolar | Buccal | 0.001 |
| Upper right canine | Distal | 0.002 |
| Upper right 1. molar | Buccal | 0.006 |
| Upper left 2. premolar | Buccal | 0.076 |
| Lower right 2. premolar | Mesial | 0.058 |
| Lower left 1. premolar | Buccal | 0.169 |
| Lower left lateral | Buccal | 0.106 |
| Upper right lateral | Distal | 0.001 |
| Lower left canine | Labial | 0.147 |

TABLE 2

Maximum ozone detectable level (ppm) after a 20 s of ozone application

| Teeth types | Sites | Ozone detection (20 s) |
|---|---|---|
| Lower left lateral | Labial | 0.137 |
| Lower left 1. premolar | Buccal | 0.177 |
| Lower right incisor | Labial | 0.069 |
| Upper right canine | Labial | 0.033 |
| Upper right lateral | Labial | 0.079 |
| Lower left 2. premolar | Buccal | 0.002 |
| Lower right 1. molar | Buccal | 0.083 |
| Upper left lateral | Labial | 0.004 |
| Lower left canine | Labial | 0.056 |
| Upper left 1. premolar | Mesial | 0.001 |

Conclusion; The use of a cup is a safe way of delivering ozone when ozone was applied for a period of either 10 s or 20 s on the root carious lesions.

EXAMPLE 2

Assessment of Maximum Ozone Levels from Extracted Teeth After the Use of Ozone for 10 s An In Vitro Test Report Study or Test: Assessment of the maximum detectable ozone levels, detected adjacent to the cup, from extracted teeth after the use of ozone for 10 s in vitro.

Purpose: To assess the maximum ozone detectable level (ppm) around a cup from the extracted teeth after a 10 s application of ozone.

1. Study or Test Protocol: 14 extracted teeth were selected. The tip of the sensor was always held within 2 mm of the edge of the cup, positioned half way between the mesial and occlusal sides of the cup. The maximum ozone detectable level (ppm) around the cup from the extracted teeth using an ozone analyser was recorded during 10 s of ozone application with the generator setting on maximum at level 10. The ozone analyser used was the API 450 model and this was calibrated by the supplier within the previous week of delivery. This device was not used for any other purpose other than this study in the interim.

The Ozone Delivery System

After plaque removal with 2 sterile cotton wool rolls, ozone gas was delivered onto the surface of each primary root carious lesion in each extracted tooth for 10 s after the lesion was dried for three seconds with a standard three in one dental syringe.

Test Results:

The maximum ozone detectable level (ppm) around the cup from the extracted teeth after a 10 s application of ozone during the treatment of root carious lesions were as shown in Table 3.

TABLE 3

Maximum ozone detectable level (ppm)

| Teeth types | Sites | Ozone detection |
|---|---|---|
| Upper incisor | Mesial | 0.005 |
| Upper lateral incisor | Labial | 0.004 |
| Upper canine | Labial | 0.003 |
| Upper 1. premolar | Mesial | 0.006 |
| Upper 2. premolar | Distal | 0.002 |
| Upper 1. molar | Buccal | 0.003 |
| Upper 2. molar | Mesial | 0 |
| Lower incisor | Lingual | 0.007 |
| Lower lateral incisor | Distal | 0.001 |
| Lower canine | Mesial | 0 |
| Lower 1. premolar | Distal | 0.009 |
| Lower 2. premolar | Lingual | 0.018 |
| Lower 1. molar | Lingual | 0.016 |
| Lower 2. molar | Mesial | 0.005 |

Conclusion: The use of a cup is a safe way of delivering ozone when ozone was applied for a period of 10 s on the root carious lesions on extracted teeth.

EXAMPLE 3

Measurement of Ozone from the Handpiece

The handpiece 16 from the ozone generator 20 was attached directly to the inlet pipe a Mini-HiCon™ the ozone detector (not shown).

| | Peak readings from Mini-HiCon ™ (g/Nm$^3$) | | | | | | |
|---|---|---|---|---|---|---|---|
| Duration (seconds) | Reading 1 (g/Nm$^3$) | Reading 2 (g/Nm$^3$) | Reading 3 (g/Nm$^3$) | Reading 4 (g/Nm$^3$) | Reading 5 (g/Nm$^3$) | Reading 6 (g/Nm$^3$) | Average (g/Nm$^3$) |
| 5 | 5.4 | 5.3 | 5.4 | 4.3 | 5.2 | 5.2 | 5.1 |
| 10 | 4.7 | 4.8 | 4.6 | 3.5 | 4.4 | 4.5 | 4.4 |

-continued

| | | | Peak readings from Mini-HiCon ™ (g/Nm³) | | | | |
|---|---|---|---|---|---|---|---|
| Duration (seconds) | Reading 1 (g/Nm³) | Reading 2 (g/Nm³) | Reading 3 (g/Nm³) | Reading 4 (g/Nm³) | Reading 5 (g/Nm³) | Reading 6 (g/Nm³) | Average (g/Nm³) |
| 20 | 4.9 | 5.9 | 6.3 | 6.3 | | | 5.9 |
| 30 | 6.3 | 6.5 | 6.3 | 6.6 | | | 6.4 |
| 60 | 6.6 | 7.0 | 7.0 | 6.7 | | | 6.8 |

| | | | Peak readings from Mini-HiCon ™ (ppm) | | | | |
|---|---|---|---|---|---|---|---|
| Duration (seconds) | Reading 1 (ppm) | Reading 2 (ppm) | Reading 3 (ppm) | Reading 4 (ppm) | Reading 5 (ppm) | Reading 6 (ppm) | Average (ppm) |
| 5 | 2522 | 2475 | 2522 | 2008 | 2428 | 2428 | 2397 |
| 10 | 2195 | 2242 | 2148 | 1635 | 2055 | 2102 | 2063 |
| 20 | 2288 | 2755 | 2942 | 2942 | | | 2732 |
| 30 | 2942 | 3036 | 2942 | 3082 | | | 3000 |
| 60 | 3082 | 3269 | 3269 | 3129 | | | 3187 |

The peak reading was obtained after about 8 seconds (even when the generator was switched on for only 5 seconds) and perhaps represented an "overshoot" before the generator/detector combination stabilized for the >20 second durations. The level then remained fairly constant at between 3.6 and 4.7 g/Nm³.

To convert from g/m³ to ppm:

The formular weight of ozone is 48 g and therefore 1 g of ozone is ¹⁄₄₈th of a mole.

The molar volume of an ideal gas (at standard temperature and pressure) is 0.0224138 m³/mol.

$$0.0224138/48 = 467 \times 10^{-6} \, m^3.$$

Therefore 1 g/m³ of ozone in air is 467 ppm.

(The ozone detector gives readings as g/Nm³ which is "normalized" to standard temperature and pressure).

Measurement of the Ozone Dissolving in a Potassium Iodide Solution

Ozone was passed through the handpiece 16, immersed in 100 ml of a 20 mM potassium iodide solution in a 250 ml conical flask covered with parafilm for the stated durations. The handpiece was then removed and the flask sealed with a neoprene bung and shaken vigorously. A 1.50 ml aliquot was removed and its electronic absorption spectrum acquired. (These measurements were taken before a diffuser was fitted.) The generator settings were: air=1, O₃=1, vac=0, red=0, regulator-setting=10.

| Duration (seconds) | $\lambda_{max}$ (351 nm) absorbance | $\lambda_{max}$ (351 nm) absorbance | $\lambda_{max}$ (351 nm) absorbance | $\lambda_{max}$ (351 nm) average absorbance |
|---|---|---|---|---|
| 1 | 0.06 | 0.08 | 0.11 | 0.08 |
| 2 | 0.50 | 0.44 | 0.26 | 0.40 |
| 3 | 0.70 | 0.56 | 0.42 | 0.56 |
| 4 | 0.77 | 0.69 | 0.50 | 0.65 |
| 5 | 0.90 | 0.84 | 0.51 | 0.75 |
| 6 | 1.08 | 0.99 | 0.68 | 0.92 |
| 7 | 1.17 | 1.11 | 0.75 | 1.01 |
| 8 | 1.30 | 1.27 | 0.95 | 1.17 |
| 9 | 1.40 | 1.40 | 1.19 | 1.33 |
| 10 | 1.57 | 1.43 | 1.38 | 1.46 |

To calculate the concentration from the peak absorbance:

$$A = E \times C \times L \text{ where}$$

L=cell path length (1 cm)

C=concentration (mol)

E=extinction coefficient

A=absorbance

E for 1M=$2.97 \times 10^4$

E for 1 μM=0.0297

C=A÷E ⇒ concentration in μmol/l is absorbance/0.0297

| Duration (seconds) | λmax absorbance (average of 3) | Concentration (μmol/l) | Total dissolved ozone (μmol) | Ozone (μg) | Volume of air/ozone mixture (ml) | Ozone in air (μg/ml = g/m$^3$) | Ozone in air (ppm) |
|---|---|---|---|---|---|---|---|
| 1 | 0.08 | 2.69 | 0.269 | 13 | 8 | 1.625 | 759 |
| 2 | 0.40 | 13.47 | 1.347 | 65 | 16 | 4.063 | 1897 |
| 3 | 0.50 | 18.86 | 1.886 | 91 | 24 | 3.792 | 1771 |
| 4 | 0.65 | 21.89 | 2.189 | 105 | 32 | 3.281 | 1532 |
| 5 | 0.75 | 25.25 | 2.525 | 121 | 40 | 3.025 | 1413 |
| 6 | 0.92 | 30.98 | 3.098 | 149 | 48 | 3.104 | 1450 |
| 7 | 1.01 | 34.39 | 3.439 | 165 | 56 | 2.946 | 1376 |
| 8 | 1.17 | 39.39 | 3.939 | 189 | 64 | 2.953 | 1379 |
| 9 | 1.33 | 44.79 | 4.479 | 215 | 72 | 2.986 | 1394 |
| 10 | 1.46 | 49.16 | 4.916 | 236 | 80 | 2.950 | 1378 |

NMR Analysis of Plaque/Caries
1. Plaque samples were obtained from volunteers and each sample was divided into two. Half of each sample was treated with ozone and half left untreated as a control.
2. The samples were each weighed. Then 600 μl of 0.5 M HClO$_4$ was added to each sample and rotamixed.
3. The samples were centrifuged and supernatants retained.
4. The samples were neutralized to a pH of between 6 and 8 and the volume of KOH used was noted.
5. The samples were centrifuged again and 600 μl of supernatant were taken for analysis.
6. 70 μl of D$_2$O and 30 μl of sodium 3-trimethylsilyl-(2,2,3,3,-$^2$H$_4$)-propionate
   (5 mM in D$_2$O) were added prior to NMR analysis.

NMR Analysis of Saliva
1. Saliva samples were obtained from volunteers and each sample was divided into two. Half of each sample was treated with ozone and half left untreated as a control.
2. The samples were centrifuged and supernatants retained.
3. 70 μl of D$_2$O and 30 μl of sodium 3-trimethylsilyl-(2,2,3,3,-$^2$H$_4$)-propionate
   (5 mM in D$_2$O) were added prior to NMR analysis.

| Iodine Standards (in 20 mM potassium iodide) | |
|---|---|
| Iodine Concentration | Absorbance at 351 nm |
| 4 uM | 0.1144 |
| 5 uM | 0.1410 |
| 7 uM | 0.1690 |
| 10 uM | 0.2002 |

EXAMPLE 4

The tray is disposed over teeth and gums with in situ orthodontic bands and ozone introduced for up to 2 minutes. Thereafter, the teeth are examined for white spots with beneficial results.

Although there has been hereinabove described apparatus for the treatment of dental caries in accordance with the present invention for the purpose of illustrating the manner in which the invention may be used to advantage, it will be appreciated that the invention is not limited thereto. Accordingly, any and all modifications, variations or equivalent arrangements which may occur to those skilled in the art, should be considered to be within the scope of the invention as defined in the appended claims.

What is claimed is:
1. A method for the treatment of white spots caused by orthodontic bands;
   disposing a resilient elastomeric tray over upper or lower teeth of a patient and orthodontic bands applied thereto, the tray being disposed with a cavity conforming to the patient's upper or lower teeth and adjacent gums;
   introducing ozone into the tray cavity through a port for a period of time to treat the white spots and sterilize said orthodontic bands;
   evacuating the ozone from the cavity; and
   removing the tray from the upper or lower teeth.
2. The method according to claim 1 wherein the period of time is less than about 2 minutes.

* * * * *